US009785802B2

(12) United States Patent
Rousseau et al.

(10) Patent No.: US 9,785,802 B2
(45) Date of Patent: Oct. 10, 2017

(54) METHOD OF DETERMINING AN AMOUNT OF ALKALINE AGENT TO BE INJECTED WITHIN THE CONTEXT OF ENHANCED OIL RECOVERY

(75) Inventors: David Rousseau, Nanterre (FR); Brigitte Bazin, Paris (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 710 days.

(21) Appl. No.: 13/994,157

(22) PCT Filed: Dec. 7, 2011

(86) PCT No.: PCT/FR2011/000641
§ 371 (c)(1),
(2), (4) Date: Aug. 7, 2013

(87) PCT Pub. No.: WO2012/080593
PCT Pub. Date: Jun. 21, 2012

(65) Prior Publication Data
US 2013/0317799 A1   Nov. 28, 2013

(30) Foreign Application Priority Data
Dec. 17, 2010 (FR) ..................... 10 04948

(51) Int. Cl.
*G06G 7/57* (2006.01)
*C09K 8/58* (2006.01)
(Continued)

(52) U.S. Cl.
CPC ............. *G06G 7/57* (2013.01); *C09K 8/58* (2013.01); *G01N 11/00* (2013.01); *G01N 15/08* (2013.01)

(58) Field of Classification Search
None
See application file for complete search history.

(56) References Cited

U.S. PATENT DOCUMENTS

| 3,871,452 A | 3/1975 | Sarem |
| 3,977,470 A | 8/1976 | Chang |
| 2005/0199395 A1 | 9/2005 | Berger |

FOREIGN PATENT DOCUMENTS

EP   2 072 752   6/2009

OTHER PUBLICATIONS

Zheng et al., Effects of Polymer Adsorption and Flow Behavior on Two-Phase Flow in Porous Media, SPE Reservoir Eval. & Eg. Society of Petroleum Engineers, vol. 3, No. 64270, Jun. 1, 2000 pp. 216-223.

(Continued)

*Primary Examiner* — Omar Fernandez Rivas
*Assistant Examiner* — Herng-Der Day
(74) *Attorney, Agent, or Firm* — Fitch Even Tabin & Flannery, LLP

(57) ABSTRACT

Method of modelling the evolution of the pH value of a porous medium after injection of an alkaline agent solution into this medium.
The alkaline agent is considered as a soda pseudo-constituent of concentration equal to an OH— concentration corresponding to the pH value of the alkaline agent solution injected. An adsorption equation calibrated to experimental data is then used to determine an amount of soda pseudo-constituent adsorbed, from the concentration of the soda pseudo-constituent. Finally, the evolution of the pH value is modelled by modelling the transport of the alkaline agent solution by means of a soda transport simulator, by replacing the soda by the soda pseudo-constituent.

2 Claims, 4 Drawing Sheets

(51) Int. Cl.
  G01N 11/00    (2006.01)
  G01N 15/08    (2006.01)

(56) References Cited

OTHER PUBLICATIONS

Bazin et al., Ion Exchange and Dissolution/Precipitation Modeling: Application to the Injection of Aqueous Fluids Into a Reservoir Sandstone, SPE Reservoir Engineering, vol. 6, No. 2, May 1991, pp. 233-238.
Schneider et al., Steady-State Measurements of Relative Permeability for Polymer/Oil Systems, Society of Petroleum Engineers Journal, Feb. 1, 1982, pp. 79-86.
Mohammadi et al., Mechanistic Modeling of Alkaline/Surfactant/Polymer Floods, SPE 110,212, Apr. 2008.
Flaaten et al., ASP Chemical Flooding Without the Need for Soft Water, SPE 116754 dated Sep. 2008.
Search Report of Appln. No. PCT/FR2011/000641 with partial English translation.

METHOD OF DETERMINING AN AMOUNT OF ALKALINE AGENT TO BE INJECTED WITHIN THE CONTEXT OF ENHANCED OIL RECOVERY

FIELD OF THE INVENTION

The field of the present invention relates to the enhanced recovery of hydrocarbons in reservoir rocks, by means of medium sweep techniques using aqueous solutions comprising chemical products.

In particular, the invention allows to determine the amounts of alkaline agent to be injected into a reservoir in order to limit the retention of a surfactant in enhanced oil recovery operations using AS (Alkaline Surfactant) or ASP (Alkaline Surfactant Polymer) methods.

BACKGROUND OF THE INVENTION

The recovery of oil from oil fields often requires injection of a displacing fluid, most often water, to maintain the pressure in the reservoir so as to allow production, through displacement of the oil in place, from injection wells to production wells arranged according to a previously optimized scheme for the field considered.

In the case of water injection, this displacing fluid can be injected alone or it can, on the contrary, contain chemical agents intended to improve sweeping of the oil in place.

Among these chemical agents, on the one hand, the surfactants are intended to reduce trapping of the oil in the pores of the rock through reduction of the water-oil interfacial tension and possibly modification of the rock wettability. On the other hand, polymers provide higher viscosity to the water, thus increasing its hydrocarbon phase sweep efficiency.

However, these two categories of enhancing products undergo losses in the reservoir due to many phenomena, among which retention or adsorption of the products on the rock, which can be high and obviously detrimental to the economic interest of such recovery methods. The presence of divalent cations in place in the reservoir water and on the rock minerals (notably clays) still increases these losses.

The most frequently used method for reducing surfactant or polymer adsorption is the injection of an alkaline additive, i.e. a base such as sodium carbonate or soda. It can in fact be shown that the adsorption of surfactants is very widely decreased to a basic pH. This effect is caused by the increase in absolute value of the (negative) surface charge of the rock due to the adsorption of the OH— ions. The basic pH is provided by the injection of the alkaline agent. In order to benefit from this effect in the surfactant injection method, one has to be able to calculate the pH value of the slug of chemical additives injected into the reservoir to limit adsorption of the surfactant.

These rock conditioning agents (alkaline agent), dissolved in various chemical forms, dissociated or not into ions, involve many chemical equilibria in aqueous phase:
  salt precipitation reactions (divalent cation salts in place notably),
  multiple interactions with the rock (ion exchange and adsorption with modification of the charges of the solid surface),
  possibly also reactions with some constituents of the oil in place (formation of soaps with the surfactant). The injection of a conditioning agent alone can even already improve the recovery of oil in relation to the conventional injection of water without any chemical agent.

All these physico-chemical phenomena have to be taken into account in order to determine the volumes and concentrations of the products to be injected, and the modes of injection (flow rates, distribution in the field via the injection scheme, etc.), for the reservoir rock conditioning phase (injection of alkaline conditioning agents) as well as for the subsequent enhanced water slugs (through surfactants and/or polymers), intended to improve the recovery and the displacement efficiency.

This dimensioning of the injected solutions is essential because it determines the feasibility and the profitability of these methods, via:
  (a) the size and the cost of the facilities: surface facilities for preparing the solutions (surfactants, polymers); number and arrangement of well pumping equipments,
  (b) the conditioning product and enhancer masses required (volumes and concentrations), therefore their cost,
  (c) and, of course, the efficiency in terms of oil recovery.

The composition of the chemical formulation (aqueous solution of chemical additives comprising surfactants, alkaline agents and polymer) is determined by laboratory experiments and by a numerical calculation for extrapolation to the size of the reservoir.

The laboratory experiments consist in injecting a formulation of chemical additives into a previously prepared reservoir core so as to represent the state of oil saturation of the reservoir prior to starting the enhanced recovery operations. During the injection of the formulation of chemical additives into the core, oil is recovered. The amount of oil recovered depends on the nature and the concentration of the additives in the formulation and on the volume of solution injected.

Numerical modelling allows to optimize the implementation of the method and to extrapolate experiments from the laboratory scale to the reservoir scale. The modelling tool is a tool allowing to account for the flows in porous media on various scales. An example of a modelling tool is the PumaFlow model (IFP Energies nouvelles, France), which is a numerical modelling tool used by reservoir engineers. In reservoir models, the flow is a two-phase flow (water/oil). The oil and water equations are of <<black oil>> type. Transport equations for each chemical species in the water phase have to be added to these <<black oil>> equations. The transport is modelled by the equation of conservation of the chemical species in the water phase. The pH value of the solution is calculated from a relation between the concentration of the alkaline agent and the OH— concentration. The alkaline agent is either directly soda or a base allowing a buffer effect to be obtained.

In the case of a buffer alkaline agent, equilibrium relations have to be associated with the previous equations to calculate the OH— concentration, then the pH value from the concentration of the buffer alkaline agent. This method is described in the following references: Pope et al. SPE 110,212 (reaction 5 for carbonate) and Pope et al. SPE 116,754 (relations 3 and 4 for metaborate). The model for a buffer alkaline agent gives satisfactory results when compared with typical experimental results, as shown in FIG. 1 that illustrates the evolution of the pH value as a function of the pore volume (VP) injected. The dots represent the experimental measurements, the curve represents the <<buffer alkaline agent>> model.

However, taking account of the equilibrium relations increases the computation times. All the thermodynamic quantities associated with the chemical equilibria also have to be known, which is difficult in particular for sodium metaborate. Furthermore, there is a risk of introducing additional uncertainties that may lead to wrong calculated pH values, or even to difficulties as regards the solution of the numerical calculation and to computation stops. In some cases (when the reservoir model has a large number of cells, or when the chemical equilibria involving the alkaline agent and allowing the OH— concentration to be calculated are not all known), it is not possible to calculate the amount of alkaline agent to be injected to prevent retention of the surfactant. It is not possible to predict the oil recovery in the method that becomes impossible to apply.

The object of the invention is a method of modelling the evolution of the pH value of a porous medium after the injection of an alkaline agent solution into this medium, without applying the system of equations relative to the equilibrium relations for the transport of the buffer alkaline agent. According to this pH modelling method, the alkaline agent is considered as a soda pseudo-constituent, of concentration equal to the OH— concentration corresponding to the pH value of the alkaline agent solution injected. The modelling tools specific to the soda compound are then used. The method according to the invention allows to calculate the amount of alkaline agent to be injected in order to obtain a basic pH in the case of a model on the reservoir scale.

SUMMARY OF THE INVENTION

In general terms, the invention relates to a method of modelling the evolution of the pH value of a porous medium after injection of an alkaline agent solution into said medium, by means of a flow simulator modelling the transportation of soda through a porous medium, characterized in that:
the alkaline agent is considered as a soda pseudo-constituent of concentration equal to an OH— concentration corresponding to the pH value of said alkaline agent solution injected,
an adsorption equation calibrated to experimental data is used to determine an amount of soda pseudo-constituent adsorbed, from the concentration of the soda pseudo-constituent,
the evolution of the pH value is modelled by modelling the transport of the alkaline agent solution by means of said soda transport simulator, by replacing the soda by the soda pseudo-constituent.

According to the invention, calibration of the adsorption equation can be performed by applying the following stages:
determining an experimental pH profile describing a pH evolution as a function of a volume of solution injected, by injecting said alkaline agent solution into a sample of said medium, and by measuring the pH value of the effluents leaving the sample,
determining a simulated pH profile by modelling the injection of alkaline agent solution into the sample by means of said simulator and of the adsorption equation,
modifying parameters of the adsorption equation until differences between said simulated profile and said experimental profile are minimized.

According to a particular embodiment, the adsorption equation has the form of a Langmuir isotherm relative to an OH— concentration. It can be written as follows:

$$C_r^{OH^-} = q_{max} \frac{k_e \cdot C_w^{OH^-}}{1 + k_e \cdot C_w^{OH^-}}$$

with:

$C_w^{OH^-}$: amount (concentration) of soda pseudo-constituent in the solution $C_r^{OH^-}$: amount (mass fraction) of soda pseudo-constituent adsorbed $q_{max}$, $k_e$: parameters of the adsorption equation to be calibrated.

The invention also relates to a method for enhanced recovery of hydrocarbons contained in an underground porous medium, by means of a technique of sweeping the medium by an aqueous solution comprising at least one chemical product, wherein an amount of alkaline agent is additionally introduced so as to limit the adsorption of said chemical product. According to this method, the amount of alkaline agent to be injected is determined by carrying out the following stages:
modelling an evolution of the pH value in said porous medium after injection of an amount of alkaline agent solution into said medium, by means of the method according to the invention,
repeating said pH evolution modelling for various amounts of alkaline agent solution injected,
selecting the amount of alkaline agent solution to be added so as to optimize the enhanced recovery of hydrocarbons.

BRIEF DESCRIPTION OF THE FIGURES

Other features and advantages of the method according to the invention will be clear from reading the description hereafter of embodiments given by way of non limitative example, with reference to the accompanying figures wherein.

DETAILED DESCRIPTION

Figure 1:
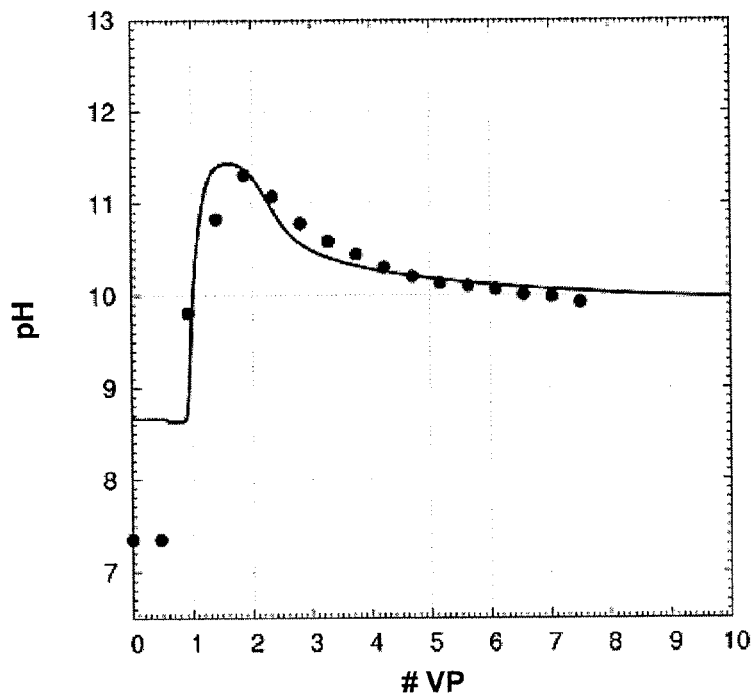
FIG. 1 shows the experimental pH points and the pH curve calculated using a complex model taking account of the equilibrium relations, <<buffer alkaline agent model>>, for the injection of 1 PV (pore volume) of 10 g/l sodium carbonate, followed by 6.5 PV chase water.

The method according to the invention is a method for enhanced recovery of hydrocarbons contained in an underground porous medium, by means of a medium sweep technique using an aqueous solution comprising at least one chemical product (surfactant, . . . ), wherein an amount of alkaline agent is additionally introduced so as to obtain a basic pH and thus to limit the adsorption of the chemical product. The invention is based on a method allowing to model the evolution of the pH value of a porous medium after the injection of an alkaline agent solution into this medium, by means of a flow simulator modelling the transport of soda through a porous medium.

According to this pH modelling method, the alkaline agent is considered as a soda pseudo-constituent, of concentration equal to the OH— concentration corresponding to the pH value of the alkaline agent solution injected. The modelling tools specific to the soda compound are then used.

The tools allowing the evolution of the pH value to be modelled after a soda injection are described hereafter.

Transport is modelled using a flow simulator modelling the transport of soda in a porous medium on different scales. An example of a modelling tool is the PumaFlow software (IFP Energies nouvelles, France). The oil and water equations are of <<black oil>> type. Transport equations for each chemical species in the water phase have to be added to these <<black oil>> equations. The equation of conservation of the chemical species in the water phase is written as follows:

$$\frac{\partial m_k}{\partial t} + div\left(\rho_w C_w^k \vec{u}_w + \vec{J}_w^k\right) + C_w^k Q_w = 0 \quad (1)$$

with:

$$m_k = \phi \rho_w S_w C_w^k + (1-\phi)\rho_r C_r^k \quad (2)$$

$$\vec{u}_w = -\frac{k k_{rw}}{\mu_w R_m}\left(\overrightarrow{grad} P_w + \vec{g}\right) \quad (3)$$

$\phi$: porosity,
k: absolute permeability of the porous medium,
$k_{rw}$: relative permeability of the water phase,
$P_w$: pressure in the water phase,
g: acceleration of gravity,
$S_w$: water saturation (w),
$\rho_w$: water density,
$\mu_w$: viscosity of water without polymer,
$\vec{u}_w$: velocity of the water phase,
$Q_w$: water injection/production flow rate,
$m_k$: total mass of component k,
$C_w^k$: mass fraction of component k in phase w (water),
$C_r^k$: mass fraction of component k adsorbed on the rock,
$\rho_r$: rock density,
$\vec{J}_w^k$: diffusive/dispersive flux of component k in phase w
where superscript k designates the chemical species: surfactant, alkaline agent and polymer.

The evolution of the pH value of the medium after soda injection is calculated using a <<soda model>>: the previous system of equations allows to calculate the transport of soda from the time when the mass fraction of soda adsorbed is defined. The adsorbed soda mass fraction follows a Langmuir isotherm relative to the OH— concentration:

$$C_r^{OH^-} = q_{max} \frac{k_e \cdot C_w^{OH^-}}{1 + k_e \cdot C_w^{OH^-}} \quad (5)$$

The pH value is then determined from the OH— concentration according to the relation:

$$pH = pKw + \log(C_w^{OH^-}) \quad (4).$$

Figure 2:
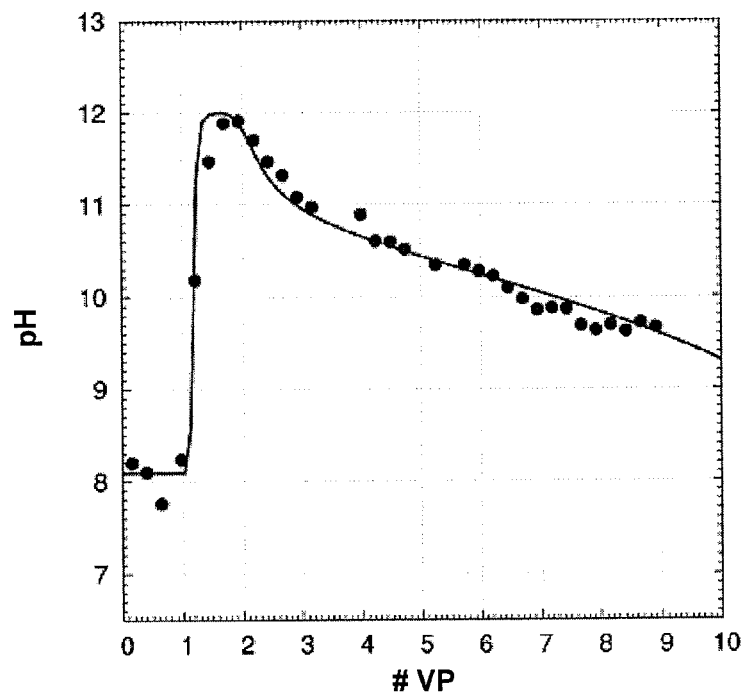
FIG. 2 shows the experimental pH points and the pH curve calculated by the <<soda model>> for the injection of 1 PV of 1 g/l soda, followed by 8 PV chase water, FIG. 3 synthetically shows the stages of an embodiment of the method according to the invention.

FIG. 2 illustrates the pH (dots) measured in the effluents during a typical experiment of soda injection as a function of the injection volume: 1 PV (pore volume) of 1 g/l soda, followed by 8 PV chase water. The curve calculated from the <<soda model>> is shown in full line. This experiment was carried out with the following stages: i) saturation with 10 g/l NaCl brine of a sandstone core; ii) injection of a volume of 10.8 ml, corresponding to 1 times the pore volume of the core (1 PV) of 1 g/l soda solution in 10 g/l NaCl brine; iii) injection of 81.6 ml (8 PV) of 10 g/l NaCl brine (referred to as <<chase water>>). It can be observed that the simulated curve (full line in FIG. 1) accounts very satisfactorily for the experimental results.

According to the invention, the numerical simulation of the injection of alkaline agent into the porous medium is achieved from this <<soda model>>, i.e. the flow simulator modelling the soda transport and the OH— ions adsorption equation.

The alkaline agent is therefore considered as a soda pseudo-constituent, of concentration equal to the OH— concentration corresponding to the pH value of the alkaline agent solution injected.

The pH value of the alkaline agent solution injected into the porous medium is thus calculated and the OH— ions concentration is deduced therefrom. The correspondence between soda concentration and buffer alkaline agent concentration is established through calculation from the thermodynamic equilibrium constants, or from pH values measured experimentally for solutions of known buffer alkaline agent concentration.

Then, in order to be able to use the flow simulator modelling the soda transport with, as the OH— ions concentration value, the previously calculated or measured one, an equation of adsorption of these soda pseudo-constituent ions is used. This equation allows to determine the amount of soda pseudo-constituent adsorbed from the soda pseudo-constituent concentration.

The adsorption equation of the soda model (Equation 5) is thus used after calibration to experimental data. The adsorption equation is thus written as follows:

$$C_r^{OH^-} = q_{max} \frac{k_e \cdot C_w^{OH^-}}{1 + k_e \cdot C_w^{OH^-}}$$

with:
$C_w^{OH^-}$: amount (concentration) of soda pseudo-constituent in the solution,
$C_r^{OH^-}$: amount (mass fraction) of soda pseudo-constituent adsorbed,
$q_{max}$, $k_e$: parameters of the adsorption equation to be calibrated.

This model is referred to as <<soda pseudo-constituent>> model.

Figure 3:
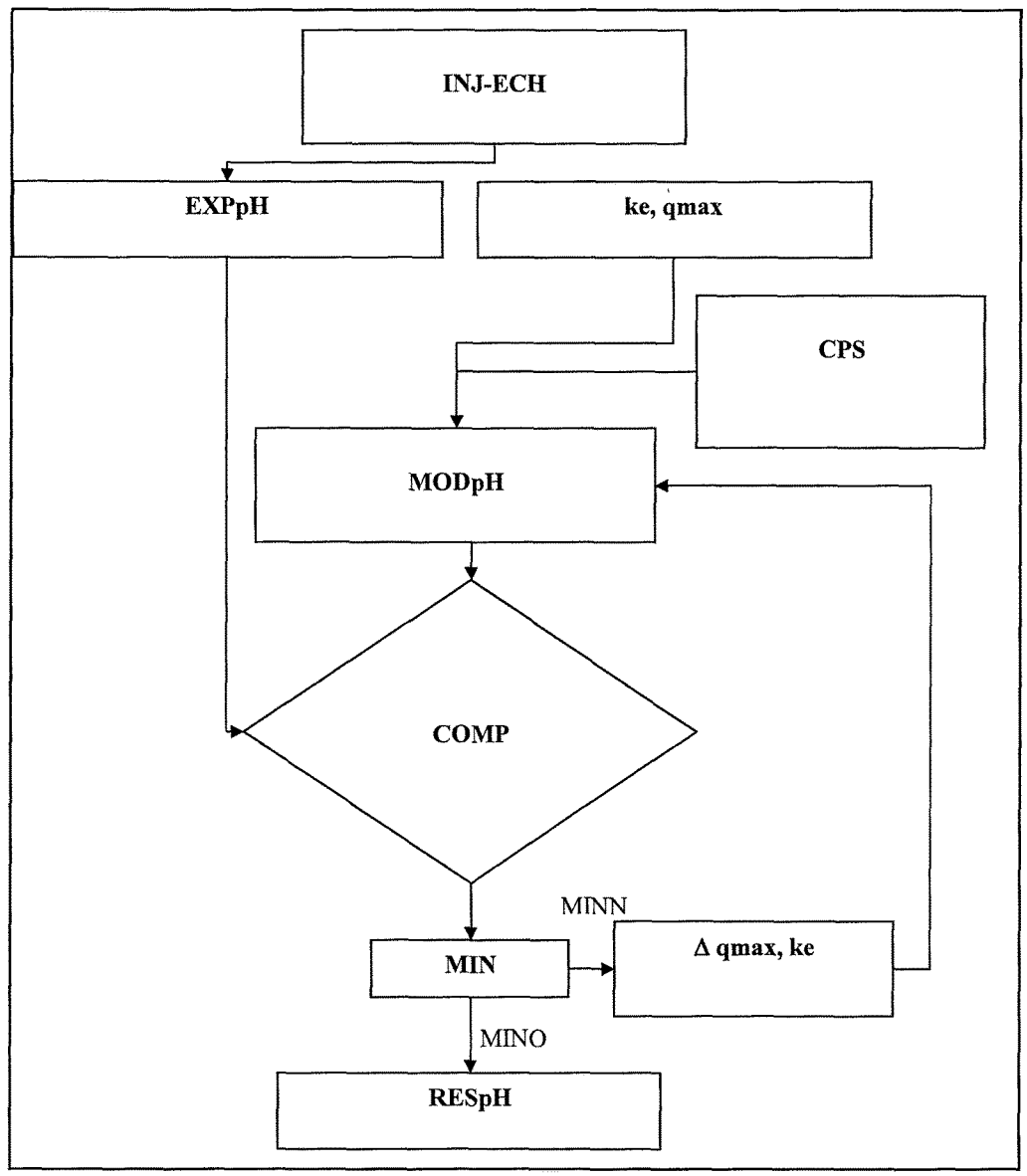

According to an embodiment, calibration can be performed using the following stages (FIG. 3):
determining an experimental pH profile: injection experiment of the alkaline agent into a sample,
modelling the experimental pH profile: solution of the alkaline agent transport equation and use of an adsorption equation.

1-Determining an Experimental pH Profile (EXPpH): Injection Experiment of the Alkaline Agent into a Sample In this stage, an experimental pH profile describing the pH evolution as a function of the volume of solution injected is determined by injecting the alkaline agent solution into a sample of the medium and by measuring the pH value of the effluents leaving the sample.

The experimental data are of the utmost importance for optimizing the injections of surfactant and alkaline chemical products in the enhanced recovery operations using chemical additive injection. Among these data, the alkaline agent adsorption isotherm is essential.

The experiment is carried out at the reservoir temperature. A sample of the reservoir rock is placed in a sample holder that can receive 5 cm-diameter and 10 cm-long cores. In order to reproduce the dynamic process operating in the reservoir, the laboratory tests are carried out under representative reservoir conditions (temperature, pressure, cores saturated with a water whose composition is identical to the water in place in the reservoir). The core is saturated with a water whose composition is identical to that of the water in place in the reservoir (referred to as water in place hereafter).

The alkaline agent solution is prepared at a concentration C (expressed in g/l hereafter) by dissolving a given mass of product in a given volume of salt water whose composition is identical to that of the water used for injection of the chemical additives into the reservoir (referred to as injection water hereafter).

The buffer alkaline agent solution is injected (INJ-ECH) at a constant flow rate. One pore volume of the buffer alkaline agent solution is generally injected. A maximum amount of 10 PV of injection water is then injected.

The effluent is collected at the core outlet in tubes. The pH value is measured in each tube. It is recorded as a function of time expressed in injected pore volumes.

A curve expressing the pH value of the effluents (fluids leaving the sample) as a function of the volume of alkaline agent solution injected through the sample is thus obtained.

2-Modelling the Experimental pH Profile (MODpH): Solution of the Alkaline Agent Transport Equation and Use of an Adsorption Equation In this stage, a simulated pH profile is determined by modelling the injection of an alkaline agent solution into the sample (laboratory experiment (stage 1)) and by determining the pH value of the corresponding effluents, by means of the <<soda pseudo-constituent>> model (simulator and adsorption equation).

The pH value of the alkaline agent solution injected into the sample (stage 1) is thus calculated and the OH— ions concentration is deduced therefrom. The correspondence between soda concentration and buffer alkaline agent concentration is established through calculation from pH values experimentally measured for solutions of known buffer alkaline agent concentration.

The soda pseudo-constituent adsorption equation is then used to determine the amount of soda pseudo-constituent adsorbed from the concentration of the soda pseudo-constituent (CPS). This equation is the adsorption equation of the soda model (Equation 5), initialized with selected values $q_{max}$ and $k_e$. These parameters are then modified.

3-Calibration of the Adsorption Equation

Calibration of the adsorption equation is performed by modifying parameters $q_{max}$ and $k_e$ of the adsorption equation until the differences between the simulated profile (stage 2) and the experimental profile (stage 1) are minimized (MIN). The experimental pH profile (EXPpH) and the modelled profile (MODpH) are thus compared (COMP). If the minimization is acceptable (MINO), calibration is stopped and the pH value is calculated on the reservoir scale (RESpH), and if the minimization is not acceptable (MINN), the procedure is repeated by modifying (Δ) parameters $q_{max}$ and $k_e$.

The model is initialized at pH=7. Several simulations (stage 2) are then carried out to calibrate the experimental curve of the pH in the effluents by modifying the two parameters $q_{max}$ and $k_e$ of the OH— pseudo-ions adsorption isotherm. The parameters of the Langmuir isotherm are thus obtained by trial and error on the experimental pH profile. This procedure is described synthetically in FIG. 3.

A transport model for the alkaline agent based on the soda model is obtained at the end of this stage. This model corresponds to the soda model where the OH— ions concentration is replaced by the soda pseudo-constituent concentration, and where parameters $q_{max}$ and $k_e$ of the OH— ions adsorption isotherm have been calibrated to the experimental data so as to provide a soda pseudo-constituent adsorption isotherm.

It is then possible to model the pH value evolution after the alkaline agent injection on the reservoir scale by modelling the transport of the alkaline agent solution using the soda transport simulator, by replacing the soda by the soda pseudo-constituent.

Simulation enables reservoir engineers to define the best reservoir development scheme by injecting sufficient amounts of alkaline agent to prevent surfactant retention. It thus allows better dimensioning of the oil recovery method using chemical additives and maximization of the oil production.

IMPLEMENTATION EXAMPLES

Two examples illustrate the capacities of the method according to the invention: the first one relates to the determination of the parameters for a sodium carbonate injection and the second to the determination of the parameters for a sodium tetraborate injection.

The conditions of each of the two injection experiments are detailed in Table 1.

TABLE 1

Sodium carbonate and sodium tetraborate injection experiments: properties of the cores used and main experimental parameters

|  | Sodium carbonate injection | Sodium tetraborate injection |
|---|---|---|
| Nature of the porous medium | Synthetic granular block 95% silica and 5% kaolinite (by mass) | Synthetic granular block 95% silica and 5% kaolinite (by mass) |
| Diameter | 2 cm | 2 cm |
| Length | 7 cm | 7 cm |
| Porosity | 25% | 25% |
| Saturation brine | NaCl 10 g/L | NaCl 10 g/L |
| Concentration of the buffer alkaline agent injected | 10 g/L | 10 g/L |
| pH value of the solution injected | 11.4 | 9.5 |
| Volume of buffer solution injected | 1 PV | 1 PV |
| Volume of chase water injected | 6.5 PV | 7 PV |
| Injection rate | 30 cm/day | 30 cm/day |

Example 1

Determining the Parameters for a Sodium Carbonate Injection

The core (synthetic granular block made up of 95 mass % silica and 5 mass % kaolinite) is initially saturated with 10 g/l NaCl brine. A volume of 5.5 ml sodium carbonate solution prepared in the same 10 g/l NaCl brine is then injected. This volume corresponds to 1 PV. After injection of this buffer solution, a volume of 35.7 ml, i.e. 6.5 PV, of 10 g/l NaCl brine (<<chase water>>) is then injected.

The sodium carbonate concentration is 10 g/l and the pH value of this solution is 11.4. The corresponding OH— ions concentration can be determined graphically from known charts, analytically from the solution of the chemical equilibria equations involved for the sodium carbonate solutions, or directly from knowledge of the pH value of the solution injected. In the case of the experiment presented, since the pH injected is 11.4, the OH— ions concentration to be used for the simulation with the <<soda pseudo-constituent model>> is $5.5 \times 10^{-3}$ mol/l. In the numerical simulations, the same injection sequences as in the experiment are carried out. In particular, the same volume of alkaline agent as in the experiment (i.e. 1 PV soda) is injected. However, the volume of chase water is set at 9 PV.

Figure 4:
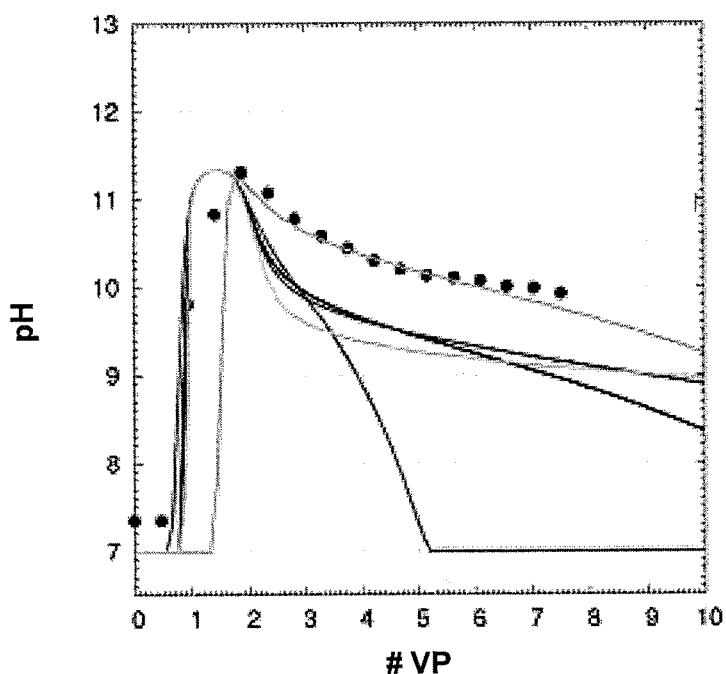
FIG. 4 illustrates the stage of determining the parameters of the OH— pseudo-ions adsorption isotherm for an injection experiment of 1 PV of 10 g/l sodium carbonate, followed by 6.5 PV chase water.

FIG. 4 shows the experimental results (dots) and the numerical results (curves) corresponding to the pH values as a function of the total volume of liquid injected. To illustrate the calibration method used, several curves are shown: each curve corresponds to the result of a simulation, performed with a pair of values $q_{max}$ and $k_e$. The calibration that is eventually selected is the simulation performed with $q_{max}=1.8$ µg/g and $k_e=900$ l/g. It promotes the good adjustment of the pH increase breakthrough. This is justified by the fact that the simulations on the reservoir scale involve injected chemical agent volumes that are always below 1 PV and chase water volumes of the order of 1 PV maximum. When the breakthrough calibration is correct, it can be observed that the simulated pH values decrease more rapidly than the experimental pH values. This is explained by the absence of buffer effect during the injection of soda alone.

Figure 5:
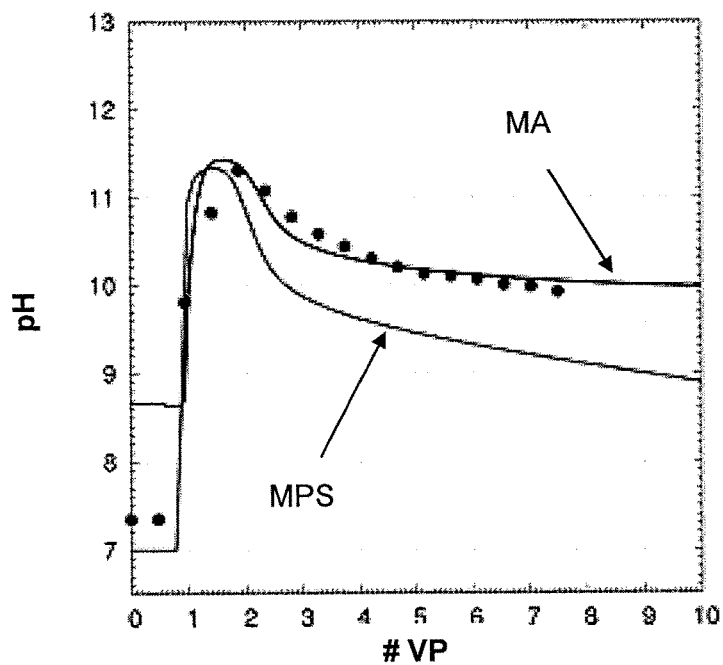
FIG. 5 shows the comparison of the <<soda pseudo-constituent model>> (MPS) using the OH— pseudo-ions adsorption isotherm and of the <<buffer alkaline agent model>> for an injection experiment of 1 PV of 10 g/l sodium carbonate, followed by 6.5 PV chase water.

A comparison between the simulation of the same sodium carbonate injection experiment with the <<soda pseudo-component model>> (MPS) and with the <<buffer alkaline agent model>> (MA) ($q_{max}=1.8$ µg/g and $k_e=900$ l/g) is given in FIG. 5. It can be observed that, if the initial pH values are not taken into account, the two simulations reproduce the experimental results satisfactorily up to about 2 PV injected, which is essential for the simulation of real cases.

Example 2

Determining the Parameters for a Sodium Tetraborate Injection

In case of an injection of complex buffer alkaline agent solutions, or having several constituents, the method according to the invention may be the only means of simulating the effect of the alkaline agent on the pH value. The experiment described by way of non limitative example relates to the injection of a 10 g/l sodium tetraborate solution with a pH value of 9.5. The other conditions of this experiment, presented in Table 1, are identical to those of the sodium carbonate injection experiment, except for the volume of chase water, which is 7 PV in the case of tetraborate.

The corresponding OH— ions concentration can be determined graphically from known charts, or directly from knowledge of the pH value of the solution injected. In the case of the experiment presented, since the pH injected is 9.5, the OH— ions concentration to be used for the simulation is $7.9 \times 10^{-5}$ mol/l. In the numerical simulations, the same injection sequences as in the experiment are carried out. In particular, the same volume of alkaline agent as in the experiment (i.e. 1 PV soda) is injected. However, as above, the volume of chase water is set at 9 PV.

Figure 6:
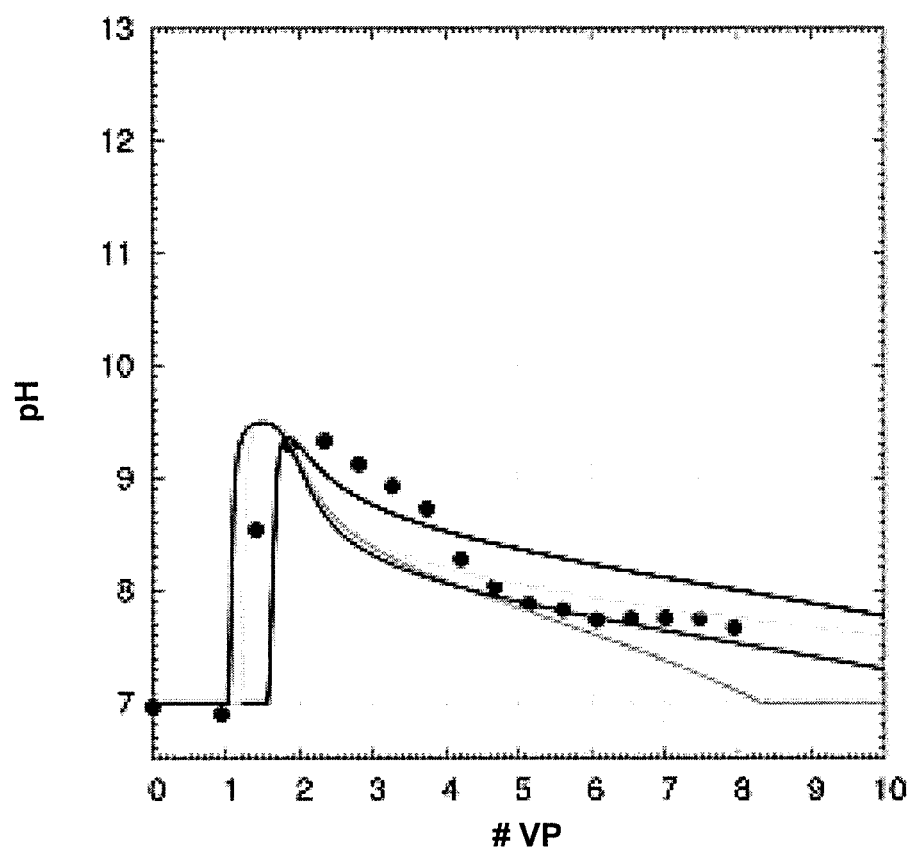
FIG. 6 illustrates the stage of determining the parameters of the OH— pseudo-ions adsorption isotherm for an injection experiment of 1 PV of 10 g/l sodium tetraborate, followed by 7 PV chase water.

FIG. 6 shows the experimental results (dots) and the numerical results (curves) corresponding to the pH values as a function of the total volume of liquid injected. To illustrate the calibration method used, several curves are shown: each curve corresponds to the result of a simulation, performed with a pair of values $q_{max}$ and $k_e$. The calibration that is eventually selected is the simulation performed with $q_{max}=0.075$ µg/g and $k_e=30,000$ l/g. As for the injection of sodium carbonate, and for the same reasons, it promotes the good adjustment of the pH increase breakthrough. It can also be observed that the difference between simulation and experiment when the pH value decreases is less marked than in the case of the sodium carbonate injection experiment. This is explained by the fact that the pH values reached are lower, the absence of buffer effect due to the injection of soda alone is also less sensitive.

Uses

The invention also relates to a method for enhanced recovery of hydrocarbons contained in an underground porous medium, by means of a medium sweep technique using an aqueous solution comprising at least one chemical product (surfactant for example), wherein an amount of alkaline agent is additionally introduced in order to limit the adsorption of this chemical product.

Dimensioning these enhancers and conditioning products injections involves calculations on a representation of the reservoir (referred to as reservoir model) discretized in form of elementary units of volume (cells) and comprises solving the equation of transport of the species in presence (water and hydrocarbon phases: oil and/or gas), the transport and the evolution of the chemical species (brought into or kept in solution, precipitated, adsorbed, converted to other chemical species). These calculations are carried out to determine the amounts of product lost in the reservoir and the recovery of oil in the production wells.

According to this method, the amount of alkaline agent to be injected is determined by carrying out the following stages:
  modelling the evolution of the pH value in the porous medium after injection of an amount of alkaline agent solution into this medium, using the method according to the invention,
  repeating modelling the evolution of the pH value for various amounts of alkaline agent solution injected,
  selecting the amount of alkaline agent solution injected leading to a decrease in the adsorption of the chemical product allowing optimum sweep of the medium.

This volume is actually a compromise between the cost and the technical performances. In fact, the larger the amount of alkaline agent injected, the more limited the adsorption, but the larger the amount injected, the higher the cost. It is therefore necessary to determine the minimum volume to be injected to obtain a sufficient adsorption decrease, i.e. providing sufficient sweep of the medium for its development to be profitable. In fact, if the amounts of surfactant retained by the rock through adsorption are significant, the efficiency of the formulation becomes very low and the amount of oil recovered becomes too small for the method to be cost-effective.

The invention claimed is:
1. A method for enhanced recovery of hydrocarbons contained in a porous medium provided underground, comprising a technique of sweeping the porous medium by an aqueous solution comprising at least one chemical product intended to improve sweeping of the porous medium, wherein an amount of a buffer alkaline agent solution comprising a buffer alkaline agent is additionally introduced so as to limit the adsorption of the at least one chemical product, characterized in that the amount of the buffer alkaline agent to be injected is determined by carrying out the following stages:

modelling an evolution of a pH value in the porous medium after injection of an amount of the buffer alkaline agent solution into the porous medium, by using a flow simulator modelling a transport of the buffer alkaline agent solution through the porous medium, characterized in that:

during the modelling, the buffer alkaline agent is considered as a soda pseudo-constituent of concentration equal to an OH— concentration corresponding to the pH value of the buffer alkaline agent solution injected, an OH— ions adsorption equation depending on parameters to be calibrated is used, this equation being calibrated to experimental data for determining an amount of soda pseudo-constituent adsorbed from the concentration of the soda pseudo-constituent, wherein the adsorption equation has the form of a Langmuir isotherm relative to an OH— concentration, the adsorption equation is written as follows:

$$C_r^{OH^-} = q_{max} \frac{k_e \cdot C_w^{OH^-}}{1 + k_e \cdot C_w^{OH^-}}$$

with:

$C_w^{OH^-}$: amount, concentration, of the soda pseudo-constituent in the buffer alkaline agent solution $C_r^{OH^-}$: amount, mass fraction, of the soda pseudo-constituent adsorbed $q_{max}$, $K_e$: parameters of the adsorption equation to be calibrated, and calibration of the adsorption equation is performed by applying the following stages:

determining an experimental pH profile describing a pH evolution as a function of a volume of solution injected, by injecting the buffer alkaline agent solution into a sample of the porous medium, and by measuring the pH value of effluents leaving the sample, determining a simulated pH profile by modelling the injection of the buffer alkaline agent solution into the sample with the flow simulator and the adsorption equation, modifying parameters of the adsorption equation until differences between the simulated profile and the experimental profile are minimized, the evolution of the pH value is modelled by modelling the transport of the buffer alkaline agent solution using the determined amount of soda pseudo-constituent adsorbed and the flow simulator, by considering the buffer alkaline agent to be the soda pseudo-constituent, repeating the modelling of an evolution of the pH value for various amounts of the buffer alkaline agent solution injected, selecting the amount of the buffer alkaline agent solution to be added so as to optimize the enhanced recovery of hydrocarbons.

2. The method according to claim 1, the simulated pH profile being further determined using the following formula (4):

$$pH = pKw = \log(C_w^{OH^-}) \quad (4).$$

* * * * *